United States Patent
Nöcker et al.

(10) Patent No.: US 7,708,785 B2
(45) Date of Patent: May 4, 2010

(54) PROCESS FOR COLOURING AND PERMANENT SHAPING KERATIN FIBRES

(75) Inventors: Bernd Nöcker, Tokyo (JP); Jonathan Wood, Weinheim (DE); Kornelia Weiβbach, Bad Soden (DE); Horst Kubatz, Alsbach-Hähnlein (DE)

(73) Assignee: KPSS-Kao Professional Salon Services GmbH, Darmstadt (DE)

(*) Notice: Subject to any disclaimer, the term of this patent is extended or adjusted under 35 U.S.C. 154(b) by 91 days.

(21) Appl. No.: 12/175,955

(22) Filed: Jul. 18, 2008

(65) Prior Publication Data

US 2009/0185993 A1    Jul. 23, 2009

(30) Foreign Application Priority Data

Jul. 30, 2007    (EP) .................................. 07014882

(51) Int. Cl.
*A61Q 5/10*    (2006.01)
(52) U.S. Cl. ...................... 8/405; 8/426; 8/455; 8/463; 8/504; 132/202; 132/208
(58) Field of Classification Search ...................... 8/405, 8/426, 455, 463, 504; 132/202, 208
See application file for complete search history.

(56) References Cited

U.S. PATENT DOCUMENTS

2006/0096042 A1* 5/2006 Schonert et al. ................ 8/406

FOREIGN PATENT DOCUMENTS

| EP | 0260716 A | 3/1988 |
|---|---|---|
| EP | 1655056 A | 5/2006 |
| EP | 1797865 A | 6/2007 |

OTHER PUBLICATIONS

English Language Abstract for EP 1 797 865 A, (Jun. 2007).

* cited by examiner

*Primary Examiner*—Eisa B Elhilo
(74) *Attorney, Agent, or Firm*—Norris, McLaughlin & Marcus

(57) ABSTRACT

A process for coloring and permanently shaping keratin fibers especially human hair comprising applying to the human hair: (a) an aqueous coloring composition based on at least one hair direct dye and not comprising any oxidative dye precursors and/or couplers, and rinsed off from hair with water after processing 1 to 45 min at a temperature of 20 to 45° C. and towel dried, (b) placing the towel dried hair on curlers, (c) applying an aqueous composition comprising at least one reducing agent and rinsed off from hair with water after a processing time of 2-30 min at ambient temperature and towel dried, (d) applying a composition comprising at least one oxidizing agent and processed for 2 to 15 min and curlers are taken off from hair and optionally rinsed off from hair with water and optionally towel dried, and (e) applying an aqueous coloring composition based on at least one hair direct dye is optionally mixed with a composition comprising at least one oxidizing agent and rinsed off from hair with water after processing 5 to 45 min at a temperature of 20 to 45° C., towel dried and dried with a dryer or left to dry in air.

17 Claims, No Drawings

PROCESS FOR COLOURING AND PERMANENT SHAPING KERATIN FIBRES

The present invention is related to a process for colouring and permanent shaping keratin fibres especially human hair in a single process.

Permanent shaping is also a common process and especially curling straight hair is used in order to increase visible hair volume.

Hair colouring is a common practice for ages. Oxidative colouration has widely been used for achieving durable, brilliant hair colour. Direct dyes, mainly of cationic character, have also found their applications for colouring hair. Recently, anionic direct dyes have as well been found to be very powerful for changing hair colour permanently and to achieve long lasting, brilliant colours in strong acidic medium. The colouring agents with anionic dyes are so formulated that the optimum conditions are realised for achieving the highest dyestuff penetration into hair. European patent application with laid open number EP 1 022 014 describes such compositions comprising anionic dyestuffs, solvents, as aid to enhance penetration of said dyestuffs, and a buffer solution to adjust the pH of the dyeing agent in the range from 2 to 6. For enhancing penetration of dyestuffs, solvents are used such as ethanol, benzyl alcohol, propylene carbonate, dipropylene glycol. Products are found on the professional hair dressing market applying this technology.

U.S. Pat. No. 5,601,620, as well, discloses hair colouring agents with acid dyes, an organic solvent and at least one polysiloxane as a conditioner. The dyeing compositions disclosed here are having a pH in the range of 1.5-4.5.

Furthermore it has long been known to colour hair using direct cationic dyes and neutral nitro dyes. The direct cationic dyes developed recently and disclosed in international patent applications WO 95/01772 A1 and WO 95/15144 A1 have proven to deliver long lasting intensive colours.

Currently these two processes, colouring and permanently shaping of keratin fibres especially human hair, are carried out separately in two independent processes in order to secure optimal and long lasting colouration and permanent shaping, especially curling. In practice a person willing to have both services is, therefore, asked to visit the hair dressing salon twice within a short period of time. In the first visit, hair is permanently shaped and after a week of two or three hair is coloured. This brings about, first of all, economical problems and secondly it is very much time intensive.

There are a few attempts made to carry out two services in a single process, in the same hair dresser visit. For example EP 1655056 A1 discloses a process for colouring and permanently shaping hair wherein oxidative colouration is carried out first and the hair is treated with an acidic treatment and after rinsing off the acidic treatment and rolling up the hair onto curlers, a keratin reducing agent is applied onto hair and processed and finally hair is fixed with an oxidizing agent and treated with an acidic treatment again, if necessary. It has been observed that with the suggested method hair is not curled very effectively and also colours so obtained lack intensity, shine and especially durability. It has further been observed that hair needs rich conditioning after such a process since considerable amount of hair damage took place.

Other than the above suggested process, it has been a long hair dressing practice to use the fixing stage of a permanent shaping process at the same time for colouring hair. It should be noted that a permanent shaping hair involves two steps. In the first step the disulfide bonds are broken by using a reducing agent in an alkaline medium and in the second stage the broken disulfide bonds are recovered using an oxidizing agent. Oxidizing agent used in a permanent shaping process usually comprises low level of oxidizing agent and more importantly does not have a strong alkaline pH, rather has an acidic pH where enough oxygen is provided to recover disulfide bonds. This is, however, quite different condition form oxidative colouring hair since there is required neutral to strong alkaline conditions and high concentration of oxidizing agent for securing intensive, homogeneous and long lasting colours.

Up until now it has not been known to colour and permanently shape keratin fibres in a single process using hair direct dyes for colouring hair.

The present invention starts from the objective in achieving excellently intensive, shiny colours and at the same time excellent permanent shaping of keratin fibres, especially curling, without damaging keratin fibres excessively.

It has surprisingly been found out when keratin fibres especially human hair is coloured and permanently shaped according to a process described below, colour intensity, brilliance and durability is excellent and hair is excellently permanently shaped. It has further been observed that hair is less damaged at the end of inventive process of the present invention.

The novel process for colouring and permanently shaping keratin fibres especially human hair according to the present invention includes the following steps:

a—an aqueous colouring composition based on at least one hair direct dye and not comprising any oxidative dye precursors and/or couplers is applied onto hair and rinsed off from hair with water after processing 1 to 45 min at a temperature of 20 to 45 20° C. and towel dried, b—the towel dried hair is put on curlers, c—an aqueous composition comprising at least one reducing agent is applied onto hair and rinsed off from hair with water after a processing time of 2 to 30 min at ambient temperature and towel dried, d—a composition comprising at least one oxidizing agent is applied onto hair processed for 2 to 15 min and curlers are taken off from hair and optionally rinsed off from hair with water and optionally towel dried, and e—an aqueous colouring composition based on at least one hair direct dye is optionally mixed with a composition comprising at least one oxidizing agent and applied onto hair and rinsed off from hair with water after processing 5 to 45 min at a temperature of 20 to 45° C. and towel dried and dried with a dryer or left to dry in the air.

Further object of the present invention is the use of the above process for colouring and permanently shaping hair in a single process.

Colouring composition used in step "a" of the above novel process comprises at least one hair direct dye. Suitable hair direct dyes are those of anionic, cationic and neutral nitro dyes. They can also be used in mixture.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15,2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

In another way of carrying out the invention, composition comprising at least one hair direct dye used in step "a" of the above novel process is mixed with an oxidizing composition comprising at least one oxidizing agent prior to application. As a rule, any oxidizing agent is suitable; the most preferred is hydrogen peroxide. Concentration of hydrogen peroxide in the composition is between 2 and 12% by weight calculated to the oxidizing composition prior to mixing.

Mixing ratio of composition comprising at least one hair direct dye used in step "a" of the above novel process and composition comprising at least one oxidizing agent is in the range of 3:1 to 1:3, preferably 2:1 to 1:2 and most preferably 1:1, by weight.

The aqueous colouring composition used in step "a" has a pH in the range of 2 to 12. In case that the colouring composition used in step "a" of the above novel process is mixed with a composition comprising at least one oxidizing agent, than pH of the composition after mixing of the two compositions preferably ranges between 5 and 12, more preferably 6.0 and 10.5 and most preferably 6.5 and 9.5 measured at room temperature.

Processing time of colouring composition in step "a" is preferably 5 to 30 min and more preferably 10 to 20 min.

The curlers can have various diameters depending on the curl diameter to be achieved and not critical for carrying out the invention. Skilled in the hair dressing art, hair dresser, can select the best suited diameter depending on customers' hair length, targeted curl intensity and finally customers' wishes.

The permanent shaping compositions used in the process according to the invention comprise at least one reducing compound at a concentration of at least 2.0% by weight calculated to total composition. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycollate, 1,2-propyleneglycol monothioglycollate (see also WO-A 93/1791), 1,3-propanediol monothioglycollate or the isomer mixture resulting therefrom, 1,3-butanediol and 1,4-butanediol monothioglycollate and the isomer mixtures therefrom, polyethylene glycol, such as di-, tri- and tetraethyleneglycol monothioglycollates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 2.0 to 15%, preferably 2.5 to 12.5% by weight, calculated to total or reducing composition.

The permanent shaping compositions containing reducing agents used in step "c" of the above process can, if necessary, comprise alkalizing agents. Their quantity is dependent on the reducing agent and the desired pH-value of the composition. Reducing agent compositions preferably contain 0.1% to 5%, in particular 0.5% to 2.5% by weight thereof, calculated to the total composition. Alkalizing agents preferred within the scope of the invention are ammonia, hydroxyalkyl amines such as monoethanol amine and triethanolamine, ammonium carbamate, ammonia and/or ammonium(bi)carbonate. It is desirable to adjust the pH-value between about 6.5 and 10.5, preferably about 7 to 9.5.

The viscosity best suited for the reducing compositions used in the above process step "c" proved to be in the range of 500 to 10,000 mPa·s, preferably about 1,000 to about 5,000 mPa·s, measured at 20° C. in a Brookfield viscosimeter (no. 5 spindle).

The viscosity is adjusted by addition of the appropriate amounts of thickening agents known per se, such as cellulose derivatives. Thickening may as well be realized by formulating a composition in form of an emulsion with the use of $C_{10}$-$C_{22}$-fatty alcohols, in admixture with long mono alkyl chain quaternary ammonium surfactants.

Composition comprising at least one oxidizing agent used in step "d" of the above novel process comprises preferably hydrogen peroxide as an oxidizing agent at a concentration of preferably 1 to 5%, more preferably 2 to 3% by weight calculated to total composition. The pH of the composition is in the range of 2 to 6, preferably 2.5 to 5, more preferably 3 to 5 and most preferably 3 to 4.5 measured at room temperature.

In the novel process of the present invention, aqueous colouring compositions used in step "e" can basically be the same composition used in step "a". Here again in another way of carrying out the invention, colouring composition is mixed with a composition comprising at least one oxidizing agent preferably hydrogen peroxide. Oxidizing composition used here is same as the one used in step a.

The aqueous colouring composition used in step "e" has a pH in the range of 2 to 12, same as the one used in step "a". In case that the colouring composition used in step "a" of the above novel process is mixed with a composition comprising at least one oxidizing agent, than pH of the composition after mixing of the two compositions preferably ranges between 5 and 12, more preferably 6.0 and 10.5 and most preferably 6.5 and 9.5 measured at room temperature.

If a further embodiment of the present invention aqueous colouring composition used in step "e" comprises further at least one oxidative dyestuff precursor and optionally at least one coupling agent. In this case, the composition must be mixed with a composition comprising at least one oxidizing agent and should have pH in the range of 5 to 12, more preferably 6.0 to 10.5 and most preferably 6.5 to 9.5 measured at room temperature and after mixing the two compositions.

As a rule any oxidative dye precursor is suitable for the purpose of the present invention. Examples to suitable oxidative dye precursors are p-phenlynediamine, p-methylaminophenol and substituted p-phenylenediamines such as 2,5-diaminotoluene, 2-n-propyl or 2-ethyl-p-phenylenediamine, 2,6-di-methyl-p-phenylenediamine, 2-(2,5-diaminophenyl) ethanol, 1-amino-4-bis-(2'-hydroxy-ethyl)aminobenzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diaminophenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxypyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

Further to the oxidative dye precursors, aqueous colouring composition applied onto hair in step "e" comprises at least one coupling agent. In general any coupling agent known in the art is suitable for the purpose of the present invention.

Suitable coupling agents are resorcinol, 2-methyl resorcinol, 4-chlororesorcinol, 2-amino-4-chlorophenol, 5-amino-4-methoxy-2-methylphenol, 3-amino-phenol, 1-methyl-2-hydroxy-4-aminobenzene, 3-N,N-dimethyl aminophenol, 2.6-dihydroxy-3.5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino) benzene, 1-amino-3-[bis(2'-hydroxy-ethyl) amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol or the water-soluble salts thereof.

Concentration of oxidation dyes precursors and coupler is customarily in the range of 0.01 to 5% by weight calculated to total composition prior to mixing.

Either colouring compositions used in steps "a" and "e" and/or reducing composition used in step "c" and/or oxidizing composition used in steps "a" "d" and "e" can comprise the following ingredients explained in detail below, unless otherwise stated.

The above mentioned compositions comprise surfactants selected from anionic, nonionic, cationic and amphoteric ones. Their proportion ranges from 0.05% to 10%, in particular from 0.1% to 5% by weight, calculated to total composition.

Suitable anionic surfactants are especially the known alkyl ether sulfates and carboxylic acids, in particular in form of their alkali salts, as well as protein fatty acid condensates.

Suitable nonionic surfactants, which are preferred within the scope of the invention, are in particular $C_8$-$C_{18}$-fatty alcohol polyglycol ethers, fatty acid polyglycol esters, fatty acid alkanolamides, amineoxides, and especially $C_8$-$C_{18}$-alkyl polyglucosides.

Also possible is the incorporation of amphoteric surfactants, such as the known alkyl betaines, alkyl amido betaines, and alkyl amphoacetates.

Further according to a further preferred embodiment, the above mentioned compositions comprise at least one cationic surfactant according to general formula

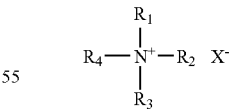

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

$R_5 CO\ NH\ (CH_2)_n$ where $R_5$ is saturated or unsaturated, branched or non-branched alkyl chain with 7-21 C atoms and n has typical value of 0-4 or

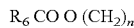
$R_6 CO\ O\ (CH_2)_n$ where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

Concentration of cationic surfactant is in the range from 0.05% to 5%, preferably 0.1% to 2.5% by weight, calculated to total composition.

Suitable long-chain quaternary ammonium compounds which can be used alone or in admixture are in particular cetyl trimethyl ammonium chloride, dimethyl dicetyl ammonium chloride, trimethyl cetyl ammonium bromide chloride, stearyl trimethyl ammonium chloride, dimethyl stearyl benzyl ammonium chloride, benzyl tetradecyl dimethyl ammonium chloride, dimethyl dihydrogenated tallow ammonium chloride, lauryl pyridinium chloride, lauryl dimethyl benzyl ammonium chloride, lauryl trimethyl ammonium chloride, tris-(oligooxyethyl) alkyl ammonium phosphate, cetyl pyridinium chloride, etc.

Additional examples to so called ester and amido quaternary ammonium compounds are distearyldimonium chloride, dipalmitoylethylhydroxyethylmonium chloride, dioleoylethyl dimethyl ammonium methosulfate, dioleoylethyl hydroxyethylmonium methosulfate, dilinolamidopropyldimonium chloride, dioleylethyl hydroxyethylmonium chloride, dipalmitoylethyldimonium chloride.

From the above quaternary ammonium compounds disclosed with the general formula, especially to mention are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially to mention are those compounds are known per se and on the market, for example, under the trade name "INCROQUAT® HO" or "OCS". These compounds are known with a general ingredient category under "amidoquat" in the cosmetic industry.

Compositions mentioned above can also comprise thickening agents to adjust the viscosity to the desired value. All known thickening agents such as anionic, non-ionic, cationic polymers are suitable for the purpose of the invention. It should be noted that compatibility with various ingredients of individual compositions should be paid attention when selecting thickening polymer. Suitable ones are cellulose derivatives such as hydroxyethyl or methyl cellulose, anionic acrylate polymers, cationic cellulose derivatives.

Thickening of the compositions can also be achieved by formulating an emulsion. In such a case at least one fatty alcohol with an alkyl chain length of 12 to 22 C atoms should be present in the composition. Examples are cetyl alcohol, stearyl alcohol or their mixture, myristyl alcohol and behenyl alcohol. Branched fatty alcohols such as octyldodecanol may also be present either alone or in mixture with kinear fatty alcohols. Emulsions must also comprise an emulsifier selected from anionic, non-ionic and cationic surfactants as mentioned above. Most preferred emulsifies are those ethoxylated fatty alcohols as nonionc ones, alkyl sulfates or alkyl ether sulfates as anionc ones and monoalkyl quaternary ammonium ones as cationic surfactants.

Further the above mentioned compositions may comprise additional cationic polymer. Basically suitable are all cationic polymers listed under the generic name "Polyquaternium" in the CTFA International Cosmetic Ingredient Dictionary. Examples are Polyquaternium 6, Polyquaternium 7, Polyquaternium 10, Polyquaternium 11, Polyquaternium 22 and Polyquaternium 28, and Polyquaternium 39.

In particular and in further preferred embodiment of the present invention, aqueous reducing composition used in step "c" of the novel process comprises further at least one copolymer of vinylpyrrolidone and quaternized vinylimidazole at a concentration in the range of 0.1 to 2.5% by weight, calculated to total composition. Preferred copolymers of vinylpyrrolidone and quaternized vinylimidazole has a charge density of at least 2 meq/g, preferably 3.0 meq/g, more preferably 6.1 meq/g at pH 7.0. Such polymers are available under the trade name Luviquat from BASF.

The cationic polymers preferred are quaternized products of graft polymers from organopolysiloxanes and polyethyl oxazolines described in EP-A 524 612 and EP-A 640 643. Such polymer is known with its CTFA name Polysilicone-9.

Concentration of one or more additional cationic polymers is in the range from 0.05% to 2.5%, preferably 0.1% to 1.5% by weight, calculated to total composition.

Further, the above mentioned composition comprise preferably at least one organic solvent. Suitable organic solvents are 2-methyl-1,3-propanediol, mono and dialcohols or the ethers thereof, in particular mono-$C_1$-$C_3$-alkyl ether, ethanol, n-propanol, isopropyl alcohol, 1-methoxypropanol, 1-ethoxypropanol and ethoxydiglycol, diols and their esters 1,3- and 1,4-butanediol, diethyleneglycol and the monomethyl and monoethyl ether thereof, dipropylene glycol and the monomethyl and monoethyl ether thereof, glycerol, hexanetriol, ethyl carbitol, benzyl alcohol, benzyloxy ethanol, propylene carbonate, N-alkyl pyrrolidone, and urea or their mixture preferably in an amount from about 0.1% to 10% by weight, calculated to the total composition.

The above mentioned compositions can comprise further ceramide type of compound such as cetyl-PG-hydroxyethylpalmitamide.

Further optional ingredient are sterols, especially the phytosterols are useful hair restructuring compounds can be present in the above mentioned compositions. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of C10 to C22 may be incorporated into the compositions of the present invention at a concentration of preferably 0.01 to 10%, preferably 0.1 to 5 and more preferably 0.2 to 2.5% by weight calculated to total composition.

It is the preferred embodiment of the present invention that oxidative colouring compositions used in steps "a" and "e" of the novel process comprise at least one saturated or unsaturated fatty acid with 12 to 22 C atoms in its molecule at a concentration of 0.1 to 10%, preferably 0.1 to 5% by weight, calculated to total composition.

Another preferred compound in the compositions mentioned above used in the novel process of the present invention is silicone compounds and especially aminated silicones such as amodimethicone available from for example Dow Corning under the brand names Dow Corning 949 Emulsion and Dow Corning 2-8194. Concentration of silicones, especially amodimethicone, is in the range of 0.05 to 2.5%, preferably 0.1 to 1% by weight calculated to total composition.

Additionally, one or more natural oil component may be incorporated into the above mentioned compositions. Suitable are such as olive oil, almond oil, avocado oil, wheatgerm oil, ricinus oil or their mixture. Concentration of these natural oil ingredients should be 0.01 to 2.5%, preferably 0.01 to 1%, more preferably 0.05 to 0.5% by weight, calculated to total composition.

Further additional compounds may be present in the above mentioned compositions of the present invention is ubichinone of the formula

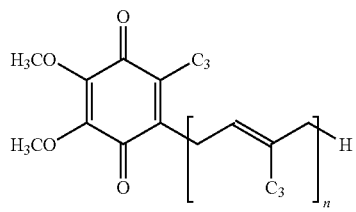

where n is a number between 1 and 10. In the preferred form of the invention at least one of the compositions mentioned above comprise at least one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

The compositions used according to the invention can naturally comprise all substances customarily found is such compositions such as fragrance, chelating agent, reducing agent in the oxidative colouring compositions for stabilizing oxidation dyes during storage, preservatives, acids or alkaline compounds used for adjusting pH, foam preventing agent sich as silicones and especially simethicone.

The following examples are to illustrate but not to limit the invention.

EXAMPLE 1

|  | % by weight |
| --- | --- |
| Colouring composition for step "a" and "e" | |
| Ext. Violet 2 (CI 60730) | 0.32 |
| Orange 4 (CI 15510) | 0.25 |
| Red 33 (CI 17200) | 0.2 |
| Yellow 10 (CI 47005) | 0.2 |
| Hydroxypropylated sachharadies | 1.5 |

-continued

|  | % by weight |
| --- | --- |
| Propylene carbonate | 25 |
| Lactic acid | q.s. to pH 2.0 |
| Fragrance, preservative | q.s. |
| Water | to 100 |
| Reducing composition for step "c" | |
| Ammonium thioglycolate (60%) | 21.3 (% by wt. |
| Ammonium hydrogen carbonate | 5.0 |
| 1,3-butylene gylcol | 3.0 |
| Polyquaternium-16* | 0.5 |
| PEG-40-Hydrogenated castor oil | 0.7 |
| Perfume | 0.4 |
| Ammonia, 25% | ad pH 8.3 |
| Water | ad 100.0 |
| Oxidizing agent for step step"d" | |
| Hydrogen peroxide | 2.5% |
| Phosphoric acid | q.s. to pH 3.5 |
| Acrylate copolymer | 0.25 |
| Water | to 100 |

Using the above composition hair was coloured and curled as follows: First, colouring composition as give above was applied onto hair and rinsed off with water after processing for 10 min at ambient temperature and towel dried. This was followed by putting hair onto curlers having a diameter of approximately 10 mm. Reducing composition was applied afterwards and processed for 15 min and rinsed off from hair and hair was towel dried. Subsequently oxidizing agent was applied onto hair and processed for 10 min at ambient temperature curlers were taken off from hair and without rinsing off same colouring composition as in step "a" was applied and rinsed off from hair after processing of 30 min at ambient temperature.

It was observed that hair was coloured into intensive natural brown shade with excellent curls.

For comparative purposed the above process was carried out wherein step "a", the first step, was omitted. It was observed that colour intensity is reduced and homogeneity of the colour was also not optimum.

EXAMPLE 2

|  | % by weight |
| --- | --- |
| Colouring composition for step "a" | |
| Stearyl alcohol | 12.0 (% by wt.) |
| Stearamide MEA | 4.0 |
| Cocamide MEA | 2.0 |
| Propylene glycol stearate SE | 4.0 |
| Sodium lauryl sulfate | 0.3 |
| Oleic acid | 2.0 |
| 1,2-Propanediol | 1.5 |
| Na-EDTA | 0.5 |
| Sodium sulfite | 1.0 |
| Ammonium bicarbonate | 0.95 |
| Ascorbic acid | 0.2 |
| Perfume | 0.4 |
| Ammonia, 25% | 8.0 |
| Ammonium chloride | 0.5 |
| Polysilicone-9 | 0.15 |
| Coenzyme Q10 | 0.001 |
| Basic red 51 | 0.5 |
| Water | ad 100.00 |

The pH of the above composition is approximately 10.5.

-continued

| | % by weight |
|---|---|
| Oxidizing agent for step step "a" | |
| Hydrogen peroxide | 6% |
| Phosphoric acid | q.s. to pH 2.5 |
| Simethicone | 0.1 |
| Acrylate copolymer | 0.25 |
| Water | to 100 |

The above compositions were mixed at a weight ratio of 2:1 (oxidative dye comprising composition and oxidizing composition) and the mixture had a pH of 9.5.

| Oxidative colouring composition for step "e" | |
|---|---|
| Stearyl alcohol | 12.0 (% by wt.) |
| Stearamide MEA | 4.0 |
| Cocamide MEA | 2.0 |
| Propylene glycol stearate SE | 4.0 |
| Sodium lauryl sulfate | 0.3 |
| Oleic acid | 2.0 |
| 1,2-Propanediol | 1.5 |
| Na-EDTA | 0.5 |
| Sodium sulfite | 1.0 |
| Ammonium bicarbonate | 0.95 |
| Ascorbic acid | 0.2 |
| Perfume | 0.4 |
| Ammonia, 25% | 1.0 |
| Ammonium chloride | 0.5 |
| Polysilicone-9 | 0.15 |
| Coenzyme Q10 | 0.001 |
| 2,5-diaminotoluene sulphate | 0.1 |
| Tetraaminopyrimidine sulphate | 2.2 |
| 2-methyl-5-hydroxyethylaminophenol | 0.1 |
| 2-methylresorcinol | 1.0 |
| 1-naphtol | 0.1 |
| Acid red 52 | 1.5 |
| Water | ad 100.00 |

The pH of the above composition is approximately 10.5 and after mixing with oxidizing agent at a weight ratio of 1 to 1 had a pH of 6.8.

Using the above composition hair was coloured and curled as follows: First, colouring composition comprising Basic red 51 was mixed with oxidizing composition for step "a" given above and applied onto hair and rinsed off with water after processing for 20 min at ambient temperature and towel dried. This was followed by putting hair onto curlers having a diameter of approximately 10 mm. Reducing composition (same as in Example 1) was applied afterwards and processed for 15 min and rinsed off from hair and hair was towel dried. Subsequently oxidizing agent (Same as in example 1) was applied onto hair and processed for 10 min at ambient temperature and curlers were taken off from hair and without rinsing off colouring composition was applied after mixing with oxidizing agent as given above and rinsed off from hair after processing of 30 min at ambient temperature. At the end it was observed that hair is coloured intensive red-violett and had excellent curl appearance.

For comparative purposed the above process was carried out wherein step "a", the first step, was omitted. It was observed that colour intensity is reduced and homogeneity of the colour was also not optimum.

Furthermore, again for the comparative purpose the step e was omitted from the above process and it was observed that the red intensity decreased significantly and hair was not homogeneously coloured.

EXAMPLE 3

Example 2 was repeated wherein following dyestuffs were used in step "a" and step "e".

| | % by weight |
|---|---|
| Dyestuff composition for step "a" | |
| 4-hydroxypropylamino-3-nitrophenol | 2.5 |
| 2-amino-6-chloro-4-nitrophenol | 0.5 |
| HC Red No. 3 | 0.2 |
| Dyestuff composition for step "e" | |
| Tetraaminopyrimidine sulphate | 2.5 |
| 2-amino-6-chloro-4-nitrophenol | 0.4 |
| Acid Red 52 | 0.9 |
| 2-methylresorcine | 1.3 |

Same process as used in example 2 was used.

It was observed that hair was coloured into shiny and intensive red copper direction and had excellent curl appearance and elasticity.

The invention claimed is:

1. Process for colouring and permanently shaping keratin fibres especially human hair comprising the following steps
   a—applying a first aqueous colouring composition based on at least one hair direct dye and not comprising any oxidative dye precursors and/or couplers onto hair rinsing off from hair with water after processing 1 to 45 min at a temperature of 20 to 45° C. and towel drying,
   b—placing the towel dried hair on curlers,
   c—applying an aqueous reducing composition comprising at least one reducing agent onto hair rinsing off from hair with water after a processing time of 2 to 30 min at ambient temperature and towel drying,
   d—applying a composition comprising at least one oxidizing agent onto hair processed for 2 to 15 min and removing curlers from hair and optionally rinsing off from hair with water and optionally towel drying, and
   e—applying a second aqueous colouring composition based on at least one hair direct dye and optionally mixed with a composition comprising at least one oxidizing agent onto hair rinsing off from hair with water after processing 5 to 45 min at a temperature of 20 to 45° C. and drying the hair.

2. Process according to claim 1 wherein the first or second colouring composition has a pH between 2 and 12.

3. Process according to claim 1 wherein at least one direct dye is selected from anionic, cationic and neutral nitro dyes.

4. Process according to claim 1 wherein the first colouring composition is mixed with a composition comprising at least one oxidizing agent.

5. Process according to claim 4 the mixture has a pH between 5 and 12.

6. Process according to claim 1 wherein the reducing composition comprises at least one reducing agent selected from the group consisting of thioglycolic acid; thiolactic acid and/or their salts; cystein and/or hydrochloride salt thereof; homocysteine; cysteamine; N-acetyl cysteine; thioglycerol; ethanediol monothioglycollate; 1,2-propyleneglycol monothioglycollate; 1,3-propanediol monothioglycollate or the isomer mixture resulting therefrom; 1,4-butanediol monothioglycollate and the isomer mixtures therefrom; polyethylene glycol; glycerol monothiolactate and further thio acids and the esters thereof; and mixtures thereof, and is present at a concentration of 2 to 15% by weight calculated to total composition.

7. Process according to claim 1 wherein reducing composition has a pH between 6.5 and 10.5.

8. Process according to claim 1 wherein the second oxidizing agent used in step "d" comprises at least one oxidizing agent at a concentration 1 to 5% by weight, calculated to total composition and has a pH between 2 and 6.

9. Process according to claim 1 wherein the second oxidative colouring composition comprises at least one oxidative dye precursor and optionally at least one coupling agent.

10. Process according to claim 1 wherein any of the compositions used in any step of the process comprises a thickening agent selected from anionic, non-ionic and cationic polymers.

11. Process according to claim 1 wherein any of the compositions used in any step of the process is an emulsion and comprises at least fatty alcohol with an alkyl chain length of 12 to 22 C atoms.

12. Process according to claim 1 wherein any of the compositions used in any step of the process comprises a surfactant selected from anionic, cationic, non-ionic and amphoteric surfactants.

13. Process according to claim 12 wherein the surfactant is a cationic surfactant according to formula

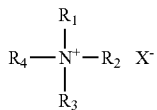

where $R_1$ s a saturated or unsaturated, branched or non-branched alkyl chain with 8-22 C atoms or

where R5 is saturated or unsaturated, branched or non-branched alkyl chain with 7-21 C atoms and n has typical value of 0-4 or

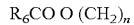

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms, and X is chloride, bromide or methosulfate.

14. Process according to claim 1 wherein any of the compositions used in any step of the process comprises at least one ubichinone of the formula

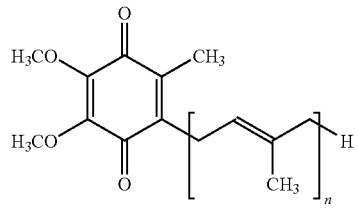

where n is a number between 1 and 10.

15. Process according to claim 1 wherein any of the compositions used in any step of the process comprises at least one organic solvent at a concentration of 0.1 to 10% by weight calculated to total composition individually.

16. Process according to claim 1 wherein any of the compositions used in any step of the process comprises at least one silicone compound.

17. Process according to claim 1 wherein any of the compositions used in any step of the process comprises at least one cationic polymer.

* * * * *